United States Patent [19]

Walker et al.

[11] 4,423,028

[45] Dec. 27, 1983

[54] CONTROL OF HOUSEFLIES BY FUMIGANT ACTIVITY

[75] Inventors: Frank H. Walker, Mill Valley; Ordell L. Wolfe, San Jose, both of Calif.

[73] Assignee: Stauffer Chemical Company, Westport, Conn.

[21] Appl. No.: 334,704

[22] Filed: Dec. 28, 1981

[51] Int. Cl.³ .................. A01N 25/06; A01N 25/18; A01N 25/20; A01N 57/00

[52] U.S. Cl. .................. 424/40; 424/215; 424/216

[58] Field of Search .................. 424/40, 215, 216

[56] References Cited

U.S. PATENT DOCUMENTS 3,042,703  7/1962  Schegk .................. 424/216

*Primary Examiner*—Stanley J. Friedman
*Attorney, Agent, or Firm*—Joel G. Ackerman

[57] ABSTRACT

This invention relates to a novel method and composition for controlling houseflies by fumigant activity by contact with the vapors of the compound O-(4-methylthiophenyl)-O,O-dimethylphosphorothioate.

4 Claims, No Drawings

CONTROL OF HOUSEFLIES BY FUMIGANT ACTIVITY

This invention relates to a method and composition for controlling houseflies by fumigant activity, that is, contact with the vapors of an insecticide compound.

Insecticides have been found which function to control insects when applied in a number of different ways. For instance, an insecticide may be sprayed onto the walls of a building or other structure to control insects by contact with residual amounts of insecticide remaining after volatile components of the sprayed mixture have evaporated. Such control is generally termed "residual spray action". Other methods of controlling insects involve, for instance, direct sprays onto insects or into areas in which insects are to be found. Such sprays may be in concentrated or dilute form and applied by various ground or air spraying techniques.

A relatively small number of insecticides have been found to control insects by what is known as fumigant activity, or fumigation. Such activity involves controlling the insects by contacting them with the insecticide in a vapor form. In one manner, used for eradicating insects inside a structure, the structure is sealed, and quantities of vapor of the insecticide are introduced into it. The vapors of the insecticide may be produced by a number of ways, for instance, by heating the insecticide, sometimes together with combustible material or volatile materials, for instance, by hot-plate or electrical coil, to vaporize the insecticide (optionally together with other ingredients in the mixture).

Another method of fumigation involves indirect contact of the insect with the insecticide and consists basically of placing an absorbent material, such as a solid fibrous support formed from a felt of wool, a cellulosic fiber material such as cotton, paper or cardboard, or a synthetic fiber, or a cardboard of glass fibers, on which the insecticide has been absorbed or supported in solid or liquid form, in an area in which insect control is desired, and permitting the insecticide to vaporize naturally, so as to produce vapors of the insecticide in the area to be controlled, which contact the undesirable insects. This is considered indirect contact as the insect does not physically contact the insecticide in its liquid or solid form.

It has now been found that the compound O-(4-methylthiophenyl)-O,O-dimethylphosphorothioate,

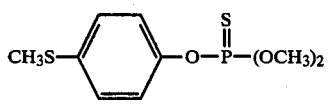

possesses the capability of controlling insects, particularly houseflies, by such fumigant, or indirect vapor, contact.

The subject compound is disclosed in U.S. Pat. No. 3,042,703 (Example 8) as one of a series of thiophosphoric acid esters having insecticidal properties. Among the other compounds disclosed in this patent is the commercial insecticide fenthion, O,O-dimethyl O-(4-methylthio-m-tolyl) phosphorothioate,

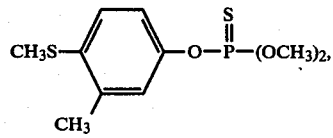

which is described in Example 1. This compound has been used to control insects in a number of ways, including residual spraying in barns and stables, and by low concentration aerial spraying to control mosquito larvae.

U.S. Pat. No. 3,042,703 states that the compounds described therein, which include both fenthion and the compound which is the subject of the present patent application, are insecticides that control, for instance, aphids, flies, mites, and lice. In general, it is stated that the compounds may be applied in rather low concentrations, including by means of aerosols. Various examples are given of the control of various insects by specific compounds encompassed by the patent disclosure. In all cases, it appears that the compounds were used in a direct contact, low concentration method, with concentrations generally being from about 0.0001 to about 0.1 percent. No indication is given in this patent that the compounds would have any effect in vapor form, and the only conclusion which could be drawn from reading it is that the compounds are contact insecticides.

EXPERIMENTAL PROCEDURE AND RESULTS

To demonstrate the unexpected vapor or fumigant activity of the subject compound, comparative tests were conducted, on houseflies, with this compound and three commercial insecticides of similar structure. The three commercial insecticides were: fenthion,

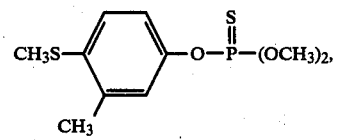

which is described earlier in this text; fenitrothion, O,O-dimethyl O-(4-nitro-m-tolyl) phosphorothioate,

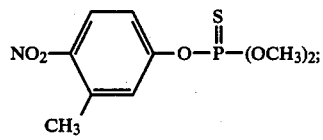

and sulprophos, O-ethyl O[4-(methylthio)phenyl] S-propyl phosphorodithioate,

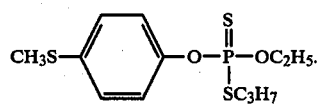

The tests were conducted in the following manner:

CONTACT RESIDUE PROCEDURE

Test compounds were diluted in acetone and aliquots pipetted onto the bottom of aluminum dishes. To ensure even spreading of the chemical on the bottom of the dishes one ml of acetone containing 0.02% peanut oil was also added to each dish. After all solvents had evaporated the dishes were placed in circular cardboard cages containing 25 female houseflies, one to two days old. The cages were covered on the bottom with cellophane and on the top with netting, and each contained a sugar-water saturated cotton plug for maintenance of the flies. Mortality was recorded after 48 hours. Test levels ranged from 100 μg/25 female houseflies down to that at which approximately 50% mortality occurred. The $LD_{50}$ values are expressed in the following Table I in terms of ug of the test compounds per 25 female houseflies.

FUMIGATION ACTIVITY PROCEDURE

Test compounds were diluted in acetone and aliquots pipetted onto 55 mm filter paper disks in the bottom of aluminum dishes. Immediately after the acetone had completely evaporated the dishes were placed in circular cardboard cages containing 25 female houseflies. The cages were sealed on both ends with cellophane and each contained a sugar-water saturated cotton plug for maintenance of the flies. A piece of netting was placed over the aluminum dish in the cage in such a way that the flies were unable to come into direct contact with the chemically treated filter paper. Mortality was recorded after 48 hours. Test levels ranged from 100 μg/25 female houseflies down to that at which approximately 50% mortality occurred. The $LD_{50}$ values are expressed in the following Table I in terms of μg of the test compound per 25 female houseflies.

TABLE I

| Compound | Contact $LD_{50}$ μ/25° flies | Fumigant $LD_{50}$ μg/25° flies/285 cc. |
|---|---|---|
| O—(4-methylthiophenyl)-O,O—dimethyl phosphorothioate | 0.85 | 2.1 |
| Fenthion | 2.9 | 14.3 |
| Fenitrothion | 4.0 | >100 |
| Sulprophos | 12.0 | >100 |

Thus, the subject compound O-(4-methylthiophenyl)-O,O-dimethyl phosphorothioate, while showing approximately four times the activity of fenitrothion in the contact tests, was at least 50 times as active as this compound as a fumigant. Fenitrothion is known to possess some, but only moderate, fumigant activity. See, for instance, U.S. Pat. No. 4,228,124. The 4-methylthiophenyl compound which is the subject of this invention surprisingly possesses an immensely improved fumigant activity with respect to fenitrothion, sulprophos, and even fenthion, which activity would not be expected from any of the information known in the art.

For use as a fumigant, the 4-methylthiophenyl compound may be incorporated in or supported on a solid porous or fibrous support. Such support may be formed, for example, by a paper, a felt of wool, cotton and/or synthetic fiber, compressed cellulose such as wood fiber, cereals, alfalfa or cotton, a felt card, a card formed from old papers, or from glass fiber.

Alternatively, the compound may be incorporated into a plastic or polymeric composition formed for instance, from a polymeric resin, plasticizer, and other typical ingredients, into which the subject compound may be introduced and the resulting composition rolled or cast out as a sheet or other solid form, or utilized as a coating medium for coating on, for instance, paper, or other material. In any or all of the above forms, the subject compound may be incorporated in a microencapsulated form or other form with adjuvants which result in slow or controlled release of the subject compound vapors into the surrounding atmosphere.

In general, in such forms, the subject compound will be present in a concentration of from about 1 to about 50 weight percent.

What is claimed is:

1. A method of controlling houseflies comprising contacting houseflies with a vapor consisting essentially of an insecticidally effective amount of O-(4-methylthiophenyl)-O,O-dimethylphosphorothioate.

2. An insecticide evaporator comprising: (a) a solid or liquid composition containing O-(4-methylthiophenyl)-O,O-dimethylphosphorothioate; and (b) a solid fibrous support absorbent for the composition (a) formed of a felt of wool, a cellulosic or synthetic material or a cardboard of glass fibers, said evaporator containing from about 1 to about 50 weight percent of the phosphorothioate of (a).

3. An insecticide evaporator comprising: (a) a solid or liquid composition containing O-(4-methylthiophenyl)-O,O-dimethylphosphorothioate; and (b) a polymeric resin dispersion or material containing from about 1 to about 50 weight percent of the compound of (a).

4. An insecticide evaporator according to claim 3 in which the phosphorothioate is incorporated in microencapsulated form with one or more adjuvants for controlled release.

* * * * *